United States Patent [19]

Johnson

[11] 4,004,583
[45] Jan. 25, 1977

[54] RESTRAINING DEVICE

[76] Inventor: Daniel E. Johnson, 2293-6th Ave., Yuma, Ariz. 85364

[22] Filed: Jan. 2, 1975

[21] Appl. No.: 538,104

[52] U.S. Cl. .............................. 128/134; 280/290
[51] Int. Cl.² ................. A61F 13/00; A62B 35/00; E05B 75/00
[58] Field of Search ........... 128/DIG. 15, 134, 133; 297/385; 119/96, 103; 280/290

[56] References Cited

UNITED STATES PATENTS

| 3,266,464 | 8/1966 | Davis | 119/103 |
|---|---|---|---|
| 3,474,781 | 10/1969 | Gaylord | 128/134 |
| 3,570,495 | 3/1971 | Wright | 128/327 |
| 3,640,273 | 2/1972 | Ray | 128/87 |
| 3,757,064 | 9/1973 | Ogawa | 297/385 |

FOREIGN PATENTS OR APPLICATIONS

| 110,868 | 7/1925 | Switzerland | 280/290 |
|---|---|---|---|
| 103,753 | 2/1917 | United Kingdom | 280/290 |

Primary Examiner—Lawrence W. Trapp
Attorney, Agent, or Firm—Bruno J. Verbeck

[57] ABSTRACT

A body restraining device for restraining movement of the body of a subject which comprises a flexible strap construction having Velcro-covered segments at the ends thereof, and also having an enlarged section of the strap construction thicker than the thickness of the strap itself, the enlarged strap section acting to prevent the strap from slipping through the space between an automobile door and the door jamb when the door is closed. The device is particularly adapted for restraining the movement of prisoners who are positioned in the jump seat of a police car or the like.

2 Claims, 2 Drawing Figures

RESTRAINING DEVICE

FIELD AND BACKGROUND OF THE INVENTION

Various restraining devices are known which have for their purpose restraining the movement of human beings who, for example, may need to be arrested by law enforcement officers. Most of these devices take the form of various wrap-around strapping construction whose end portions have affixed thereto portions of Velcro fasteners, this being a type of fastener manufactured by Velcro Corporation, New York, N.Y., which is characterized in being formed of tapes of fabrics such as nylon, one face of which comprises numerous loops and the other, complementary, face being formed of hooks. When pressed together the complementary faces become fastened to each other very securely. The prior art devices with which I am familiar are comparatively complicated, difficult to apply to a subject who may be violent, and do not permit adequate maintenance of restraint on the prisoner as when he is positioned in the jump seat of a police car.

BRIEF DESCRIPTION OF THE INVENTION

One of the principal objects of the present invention is to simplify restraining a prisoner or his apprehension, and also to effect a restraining characteristic on the prisoner when he is placed, for example, in the seat next to the drivers seat of a police car. The present invention substantially and effectually inhibits sidewise movement of the prisoner away from the closed or locked door of the vehicle and can be used to restrain the upper torso as well as the foot portion of the prisoner. The latter is particularly important since it prevents the prisoner from kicking out at the person sitting next to him.

DESCRIPTION OF A PREFERRED EMBODIMENT

Figure 1:
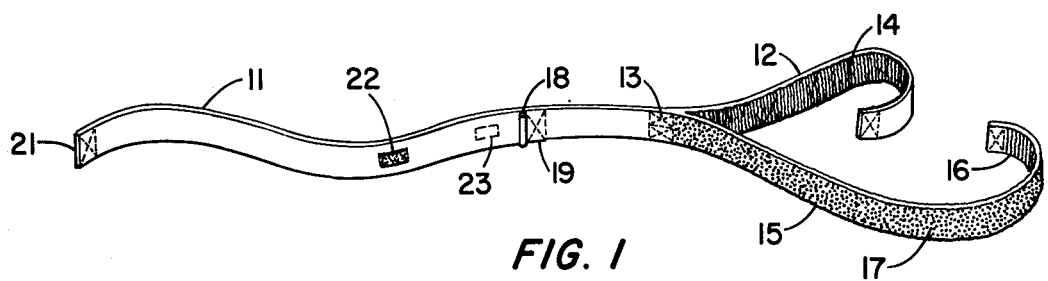
FIG. 1 is a view of the restraining device of the present invention in more or less extended form.
Figure 2:
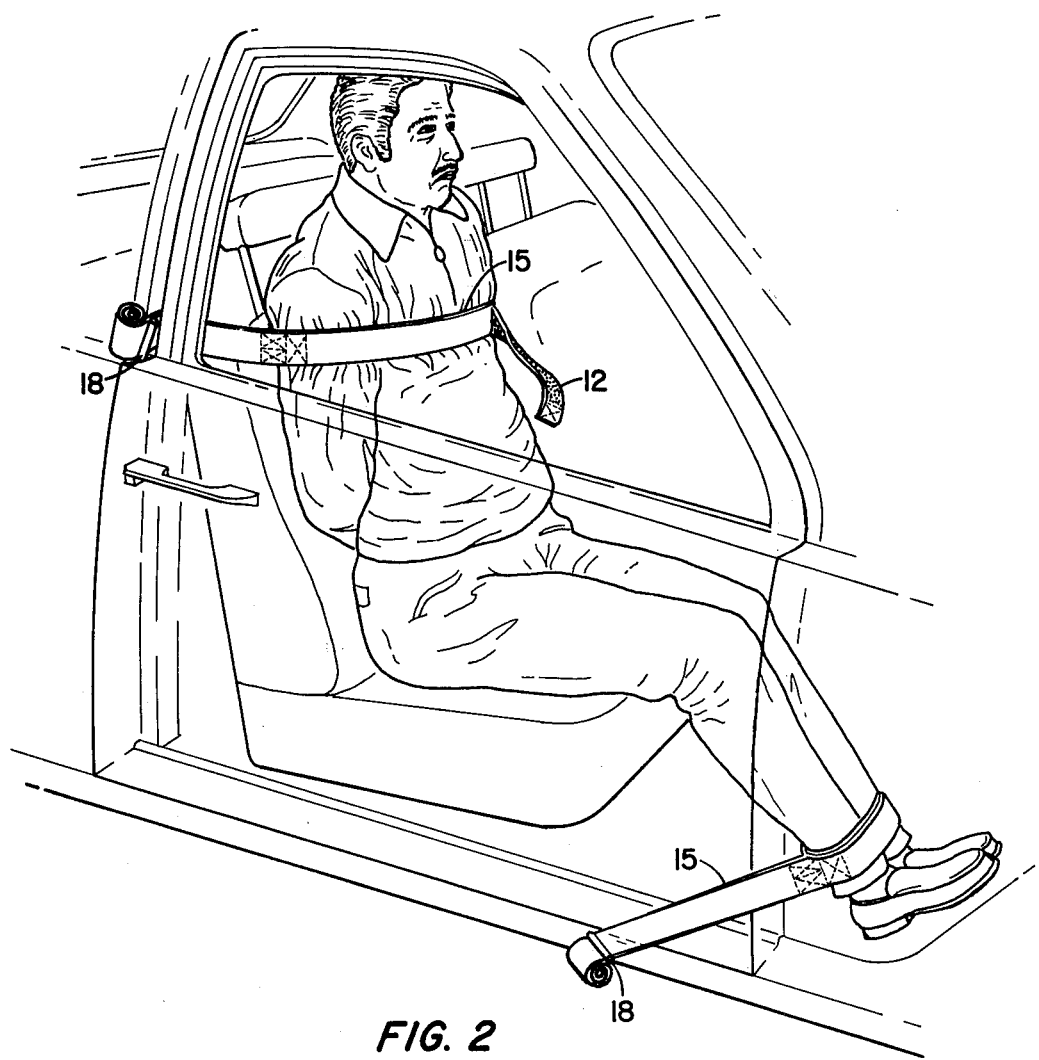
FIG. 2 is a diagramatic prespective view of a prisoner shown seated in the jump seat of a police car with a portion of the door cut away, and restrained with the device of my invention.

Referring now to the drawings, the restraining strap construction of the present invention comprises a web of nylon or the like. Sewn to the strap 11 is a second, similar strap 12, the two being joined together by sewing at juncture 13. If the strap construction is to be used around the ankles, as shown in FIG. 2, strap 12 may, conveniently, be about 18 inches long from the juncture at 13 to the end. For convenience these straps may be, for example, 2 to 3 inches wide and of stout belting material of the type used for seat belts. One face of strap 12 has sewn to it a Velcro fastener material 14 of the hook type. The end 15 of strap 11 is preferably longer than the corresponding end portion of strap 12, and may be about 24 inches in length from juncture 13 to the end. End portion 15 is covered on both faces with Velcro material. The side 16 which is in facing relationship with that side of belt segment 12 which is covered with Velcro material of the hook type is also covered with hook type Velcro material. The other side 17 of belt portion 15 is covered with the complementary form, namely the loop form, of the Velcro material. A loop is formed as at 18 by folding over and sewing a portion of the belt onto itself leaving a hole or space, into which is placed a piece of rubber or the like in the form of a rod, ⅜ to ½ inches in diameter. Such a rod is snuggly held within the loop, which loop is formed as above mentioned by sewing together as at 19 looped over portions of the belt. Somewhat away from the loop 18 are sewn, or otherwise secured to opposite faces of the belt 11, complementary pieces of Velcro material 22 and 23 one on each side of the belt 11 and spaced apart from each other, lengthwise. The two pieces of Velcro material are so spaced that when the end 21 of the belt is rolled up sufficiently, the complementary portions 22 and 23 of Velcro material keep the rolled-up loop in a "rolled up" form, for ease in packaging and storing the construction.

A restraining strap which is to be used around the upper torso and arms as shown in FIG. 2 will be like that described above except that the combined length of straps 12 and 15 should be sufficient to encircle the upper torso and arms and have an overlap of, for example, 6 to 18 inches or longer as may be desired. Other factors being equal, the greater the overlap the greater the restraining power of the device.

In applying the construction to a prisoner, it is preferable that two or more of my restraining devices be used, especially if the prisoner is to be transported as in a police car.

In applying the device to a prisoner one end of the restraining device 15 is placed around his or her upper torso and arms as shown, and then the opposite end 12 is brought around so that the loop or hook portion engages the complementary Velcro fastener of segment 15. This is done so that the fit is tight and snug. The same manipulation is done in placing the restraining device around a prisoners ankles, as best shown in FIG. 2.

With the prisoner in the jump-seat of the police car the end 21 of the strap 11 is held outside the door of the car in such a way that the loop 18 is also outside the car door; the door is slammed shut, and the end 21 may be rolled up as shown in FIG. 2. In this position the prisoner is restrained from any substantial lateral movement of his upper torso, and of his feet, and is unable to bump or kick the police officer who may be driving the car. For additional security the conventional seat belts and shoulder belts may also be applied to the prisoner.

One of the particular advantages of my invention is the ease with which the device can be applied to and removed from the prisoner, and without injury to the prisoner. This is not always the case where restraining devices which contain, for example, metallic or other hard objects are involved. This is an important consideration in situations, for example, in an accident involving the police car with the prisoner inside it, the prisoner can be removed quickly from the car without injury being caused by the restraining device. Accordingly, it is apparent that the device of my invention is simple, economical, easily applied to and removed from a person whose actions are to be restrained and is unique and distinctive over the prior art.

While I have described a presently preferred embodiment of my invention, and have disclosed and described it in detail, it will be, of course, obvious that my invention is not to be limited thereto or thereby, but only by that of the appended claims.

I claim:

1. A restraining device of the character described comprising a first flexible strap, a second flexible strap secured at one end to said first strap intermediate the ends of said first strap, said first strap having secured to one face of that end portion which is contiguous with the second strap, a tape of one complementary part of a hook-loop fastener, said second strap having secured to that face which is in facing relationship with the said tape-covered portion of said first strap a similar complementary part of a hook-loop fastener, the opposite face of said second strap having secured thereto a tape of the complementary part of a hook-loop fastener, and an enlarged segment of said first strap, substantially thicker than the thickness of said strap and located away from the juncture of the said first and second straps and from the hook-loop fastener thereof, said first strap extending beyond said enlarged segment and away from said hook-loop covered strap portion.

2. The device of claim 1 wherein said extension of said first flexible strap has on opposite sides, and spaced apart lengthwise of the strap, complementary hook-loop fastener portions.

* * * * *